(12) United States Patent
Cannon et al.

(10) Patent No.: US 7,678,094 B1
(45) Date of Patent: Mar. 16, 2010

(54) REUSABLE SWIM DIAPER

(76) Inventors: Becky B. Cannon, 6 Chiles Ave., Asheville, NC (US) 28803; Emi Kubota, 6 Chiles Ave., Asheville, NC (US) 28803

( * ) Notice: Subject to any disclaimer, the term of this patent is extended or adjusted under 35 U.S.C. 154(b) by 702 days.

(21) Appl. No.: 11/583,367

(22) Filed: Oct. 18, 2006

(51) Int. Cl.
*A61F 13/15* (2006.01)
*A61F 13/20* (2006.01)

(52) U.S. Cl. .................. 604/385.15; 604/378

(58) Field of Classification Search .......... 604/393, 604/385.15; 2/78.3, 237, 403, 404
See application file for complete search history.

(56) References Cited

U.S. PATENT DOCUMENTS

| | | | |
|---|---|---|---|
| 4,275,105 A * | 6/1981 | Boyd et al. ............. | 428/198 |
| 4,643,728 A | 2/1987 | Karami | |
| 5,146,630 A * | 9/1992 | Richard ................. | 2/181 |
| 5,354,289 A | 10/1994 | Mitchell et al. | |
| 5,542,940 A * | 8/1996 | Jonker .................. | 604/367 |
| 5,561,858 A | 10/1996 | Poirier | |
| D377,980 S | 2/1997 | Slingland | |
| 6,177,607 B1 | 1/2001 | Blaney et al. | |
| 6,195,800 B1 | 3/2001 | Gilmer et al. | |
| 6,350,257 B1 * | 2/2002 | Bjorklund et al. ....... | 604/385.01 |
| 6,487,727 B1 * | 12/2002 | Harsant ................. | 2/400 |
| 6,583,331 B1 | 6/2003 | McCormack et al. | |
| D478,169 S | 8/2003 | Sosalla | |
| 6,652,504 B1 | 11/2003 | Olson et al. | |
| 6,663,611 B2 | 12/2003 | Blaney et al. | |
| 6,673,980 B1 | 1/2004 | Varona et al. | |
| 6,797,856 B1 | 9/2004 | Kolb et al. | |
| 6,822,135 B2 | 11/2004 | Soerens et al. | |
| 6,848,121 B1 * | 2/2005 | Halid .................... | 2/400 |
| 6,852,905 B2 | 2/2005 | Baker | |
| 6,996,851 B2 | 2/2006 | Nordness et al. | |
| 7,011,653 B2 | 3/2006 | Imsangjan et al. | |
| 7,047,572 B2 | 5/2006 | Hopkins | |

(Continued)

FOREIGN PATENT DOCUMENTS

JP 2005000537 A 1/2005

(Continued)

OTHER PUBLICATIONS i Play® non-disposable swim diapers which "have a lightly absorbent inside layer with a snug-fitting waterproof Poly Lycra® outside layer," from Bambino Mountain website www/bambinomountain.com/IP224.html (effective date unknown).

*Primary Examiner*—Melanie J Hand
(74) *Attorney, Agent, or Firm*—Carter, Schnedler & Warnock, P.A.

(57) ABSTRACT

A reusable swim diaper, which includes a main torso part having an extent defined by an elastic banded torso receiving aperture at its upper end for receiving a torso, a pair of elastic banded leg receiving apertures at its lower end, and a crotch portion generally between said leg receiving apertures. The main torso part includes a bodyside inner layer of breathable wick away fabric having an extent corresponding to the extent of the main torso part, an absorbent terry cloth intermediate layer, and a waterproof outer layer having an extent corresponding to the extent of said main torso part. The layers are made of materials which are capable of withstanding laundering and are restored to substantially their original conditions by laundering.

19 Claims, 4 Drawing Sheets

U.S. PATENT DOCUMENTS

2004/0254555 A1   12/2004  Wang et al.
2005/0069672 A1 *  3/2005  Katsin ......................... 428/88
2005/0081275 A1 *  4/2005  Galvao ........................... 2/67
2007/0256261 A1 * 11/2007  Benitez et al. ................ 15/118

FOREIGN PATENT DOCUMENTS

WO    WO 2005/004772  A1   1/2005

* cited by examiner

REUSABLE SWIM DIAPER

BACKGROUND OF THE INVENTION

The invention relates to so-called waterproof swim diapers, to be worn by infants and young children.

SUMMARY OF THE INVENTION

In one aspect, a reusable swim diaper is provided, which includes a main torso part having an extent defined by an elastic-banded torso-receiving aperture at its upper end for receiving a torso, a pair of elastic-banded leg-receiving apertures at its lower end, and a crotch portion generally between said leg receiving apertures. The main torso part includes a bodyside inner layer of breathable wick-away fabric having an extent corresponding to the extent of the main torso part, an absorbent terry cloth intermediate layer, and a waterproof outer layer having an extent corresponding to the extent of said main torso part. The layers are made of materials which are capable of withstanding laundering and are restored to substantially their original conditions by laundering.

In another aspect, a reusable swim diaper is provided, which includes a main torso part having an extent defined by an elastic-banded torso-receiving aperture at its upper end for receiving a torso, a pair of elastic-banded leg-receiving apertures at its lower end, and a crotch portion generally between said leg receiving apertures. The main torso part includes a bodyside inner layer of breathable wick-away fabric having an extent corresponding to the extent of the main torso part, an absorbent terry cloth intermediate layer comprising a polyester/polyamide fiber blend and having a fabric weight of approximately 640 g/m$^2$, and a waterproof outer layer having an extent corresponding to the extent of said main torso part. The layers are made of materials which are capable of withstanding laundering and are restored to substantially their original conditions by laundering.

DETAILED DESCRIPTION

Figure 1:
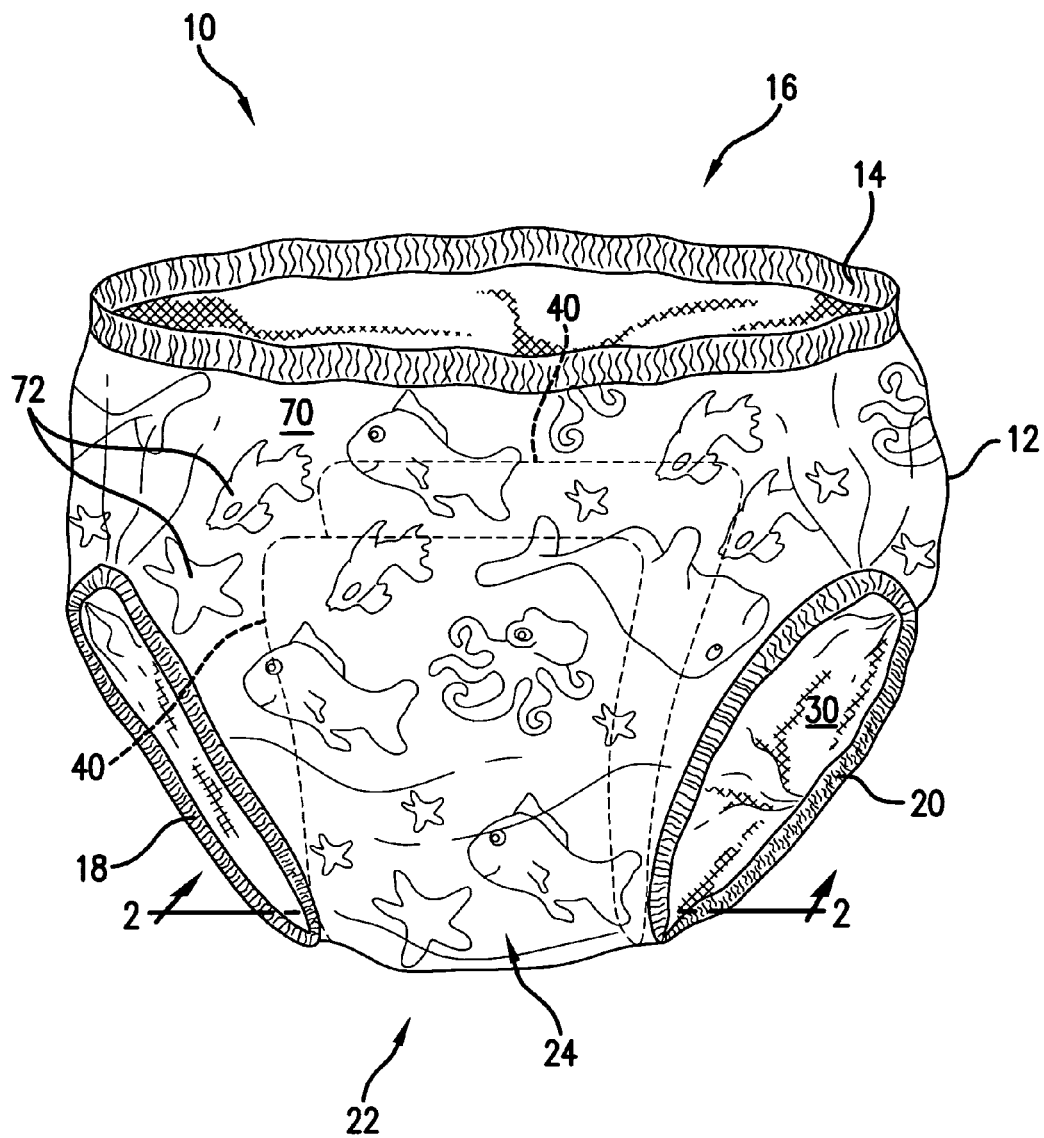
FIG. 1 is a three-dimensional view of a first embodiment of a swim diaper embodying the invention.
Figure 2:
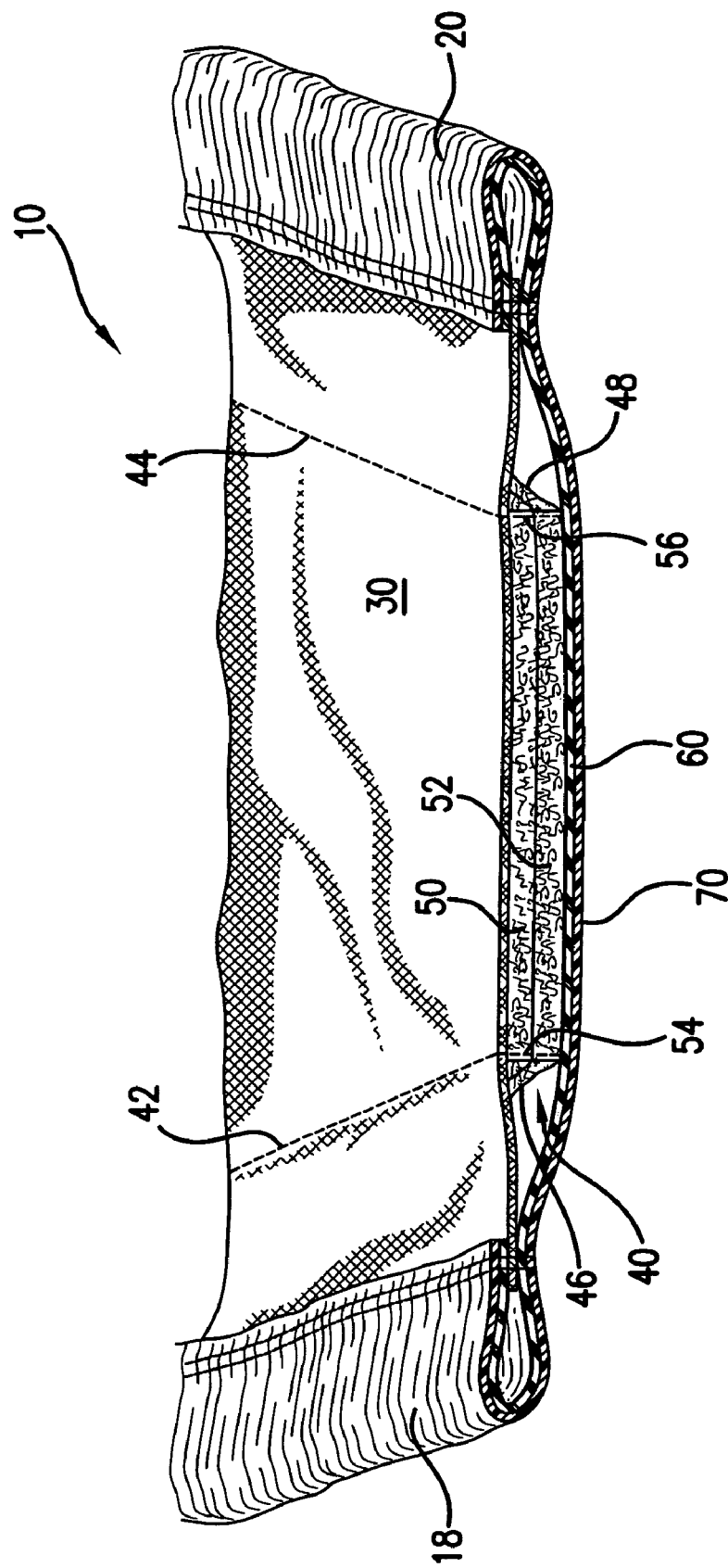
FIG. 2 is a cross-sectional view taken on line 2-2 of FIG. 1.

FIGS. 1 and 2 depict a swim diaper 10 of brief configuration embodying the invention. The swim diaper 10 includes a main torso part 12 having an extent defined by an elastic-banded torso-receiving aperture 14 at its upper end 16, and a pair of elastic-banded leg-receiving apertures 18 and 20 at its lower end 22. A crotch portion 24 is generally between the leg-receiving apertures 18 and 20.

The main torso part 12 is of multiple-layer construction, and includes a bodyside inner layer 30 of breathable wick-away fabric. A suitable breathable wick-away fabric is a knitted polyester fabric. The bodyside inner layer 30 has an extent corresponding to the extent of the main torso part 12 itself, and accordingly is also defined by the torso-receiving aperture 14 and the leg-receiving apertures 18 and 20. The bodyside inner layer 30 is sewn at the edges of the apertures 14, 18 and 20.

Adjacent the bodyside inner layer 30 is an absorbent terrycloth intermediate layer 40. In the embodiment of FIGS. 1 and 2, the absorbent terrycloth intermediate layer 40 has an extent corresponding to the crotch portion 24 of the main torso part 12. A suitable material for the absorbent terrycloth intermediate layer 40 is a polyester/polyamide fiber blend.

It is important that the terrycloth intermediate layer 40 have sufficient absorbency to absorb an anticipated volume of urine. In the illustrated embodiment, the absorbent terrycloth intermediate layer has a fabric weight of approximately 640 g/m$^2$, and is approximately 7 cm×28 cm in size (if laid flat). The area of the absorbent terrycloth intermediate layer 40 is accordingly approximately 200 cm$^2$ (rounded up from 196 cm$^2$). The absorbent terrycloth intermediate layer 40 is sewn to the bodyside inner layer 30 along two stitching lines 42 and 44 immediately adjacent lateral edges 46 and 48 of the intermediate layer 40.

Rather than a single layer having a fabric weight of approximately 640 g/m$^2$, and particularly in view of the availability of stock materials, the absorbent terrycloth intermediate layer 40 takes the form of two sublayers 50 and 52, each having a fabric weight of approximately order of 320 g/m$^2$. Stitches 54 and 56 extend through both sublayers 50 and 52, as well as through the bodyside inner layer 30.

Rather than a single layer having a fabric weight in the order of 640 g/m$^2$, and particularly in view of the availability of stock materials, the absorbent terrycloth intermediate layer 40 takes the form of two sublayers 50 and 52, each having a fabric weight in the order of 320 g/m$^2$. Stitches 54 and 56 extend through both sublayers 50 and 52, as well as through the bodyside inner layer 30.

Still referring to FIGS. 1 and 2, the main torso part 12 additionally has a waterproof outer layer 60, which also has an extent corresponding to the extent of the main torso part 12. The waterproof outer layer 60 is sewn at the edges of the torso-receiving aperture 14 and the leg-receiving apertures 18 and 20. A suitable material for the waterproof outer layer 60 is a coated woven nylon fabric. The waterproof outer layer 60, in combination with the elastic-banded apertures 14, 18 and 20, serves to minimize the flow of liquids, such as urine and swimming pool water, between the inside and the outside of the swim diaper 10, particularly between the absorbent terrycloth intermediate layer 40 and the outside environment.

For appearance purposes, the swim diaper 10 of FIGS. 1 and 2 additionally includes a decorative fabric visible layer 70, including representative decorative designs 72 printed thereon. The decorative fabric visible layer 70 can be of any suitable fabric, such as a nylon fabric. In the brief configuration embodiment 10 of FIGS. 1 and 2, the decorative fabric visible layer 70 has an extent corresponding to the extent of the main torso part 12, and is sewn to the main torso part 12 at the edge of the torso-receiving aperture 14, as well as at the edges of the leg-receiving apertures.

Significantly, all of the layers, the bodyside inner layer 30, the absorbent terrycloth intermediate layer 40, the waterproof outer layer 60 and the decorative fabric visible layer 70 are made of materials which are capable of withstanding laundering, and are restored to substantially their original condition by laundering. Thus, the swim diaper 10 is reusable, in contrast to disposable swim diapers. The swim diaper 10 is viewed as any other garment which is regularly laundered and worn again.

Figure 3:
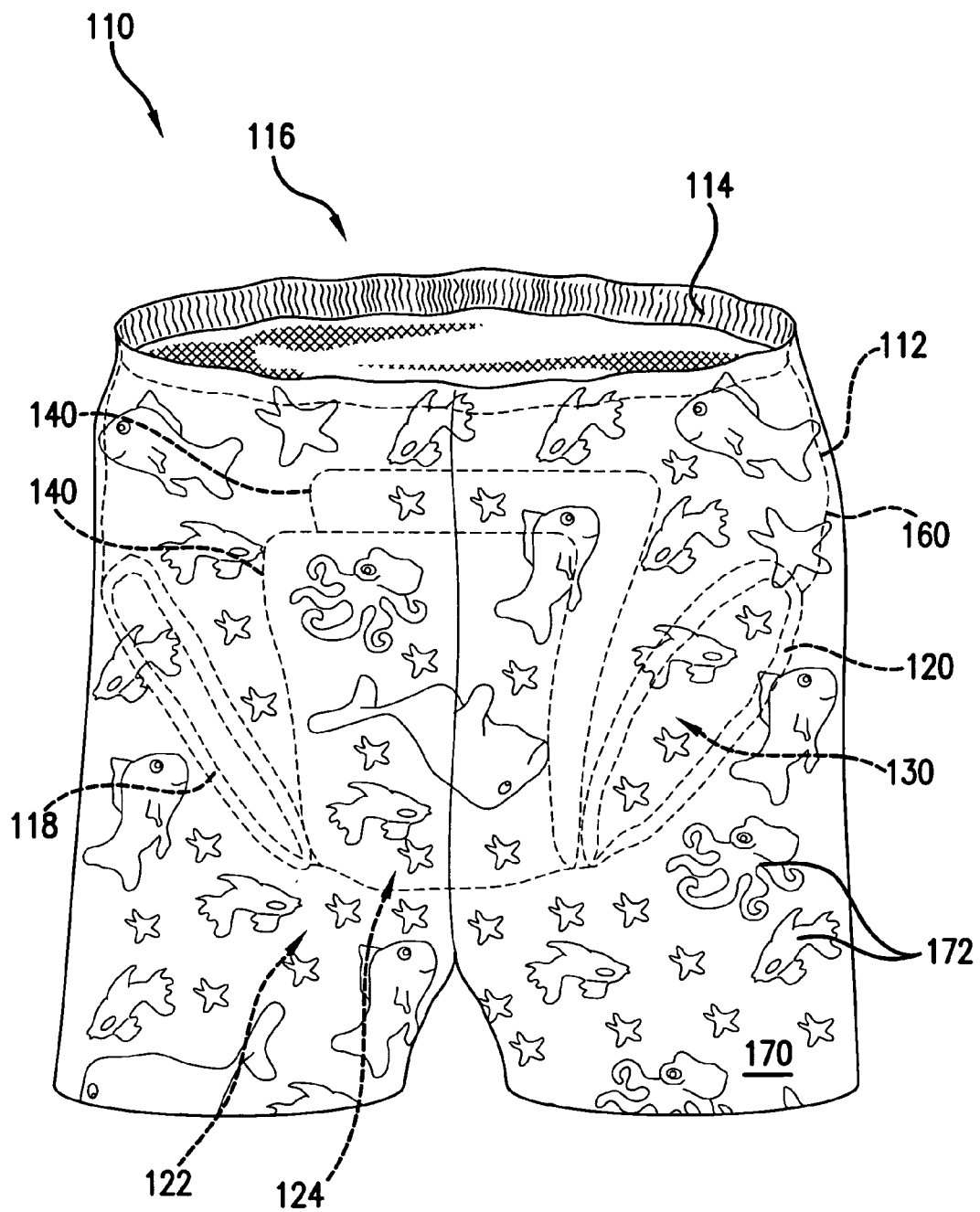
FIG. 3 is a three-dimensional view of a second embodiment of a swim diaper embodying the invention.
Figure 4:
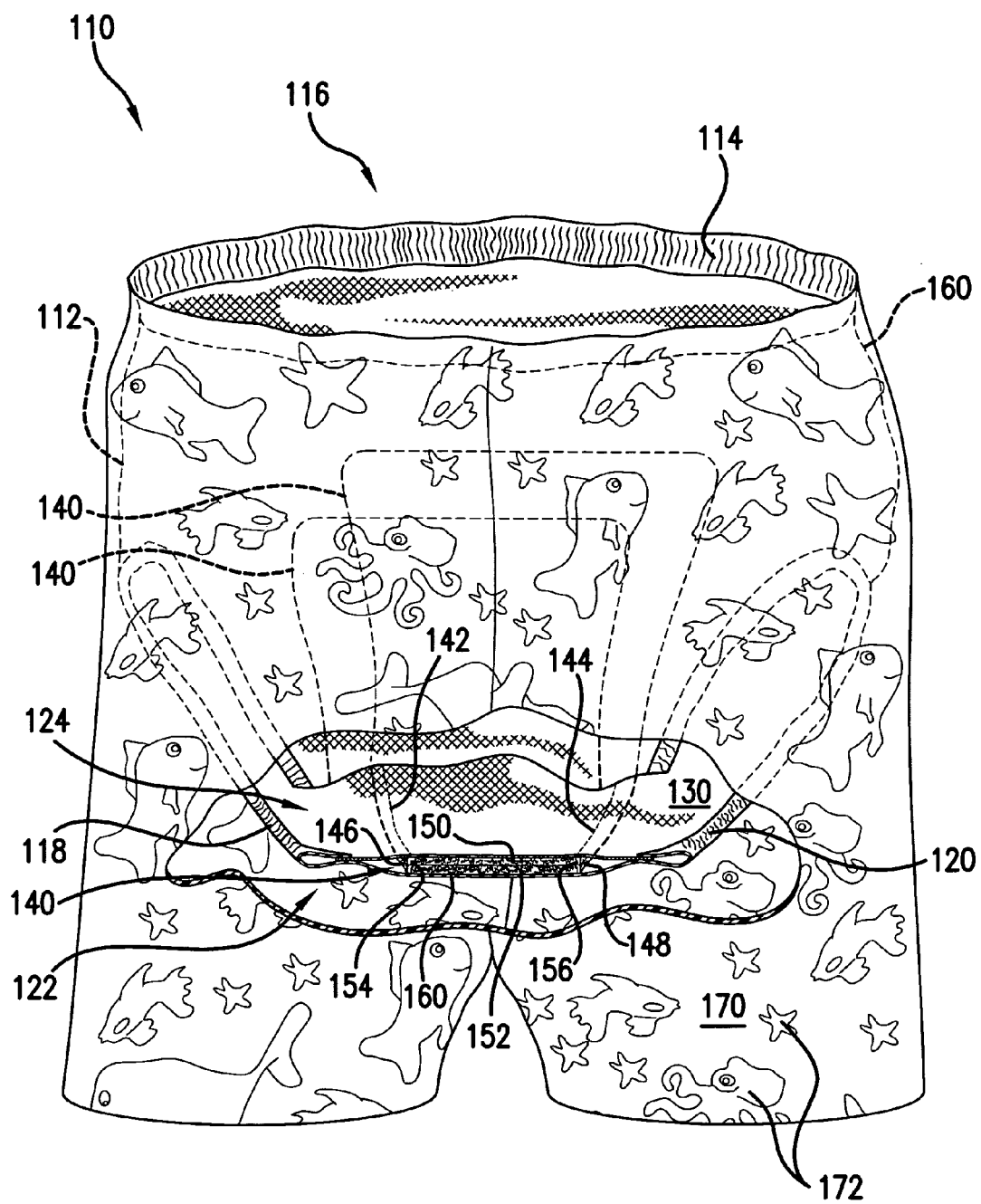
FIG. 4 is a three-dimensional view of the swim diaper of FIG. 3, partly cut away and partly in cross-section.

With reference now to FIGS. 3 and 4, another swim diaper 110 embodying the invention is of boxer short configuration. The swim diaper 110 has a main torso part 112 which is of multiple-layer construction and basically identical to the main torso part 12 of the swim diaper of FIGS. 1 and 2. The main torso part 112 in the swim diaper 110 of FIGS. 3 and 4 has an extent defined by an elastic-banded torso-receiving aperture 114 at its upper end 116, and a pair of elastic-banded leg-receiving apertures 118 and 120 at its lower end 122. A crotch portion 124 is generally between the leg-receiving apertures 118 and 120. A bodyside inner layer 130 of breathable wick-away fabric has an extent corresponding to the extent of the main torso part 120, is defined by a torso-receiving aperture 114 and the leg-receiving apertures 118 and 120, and is sewn at the edges of the apertures 114, 118 and 120. Adjacent the bodyside inner layer 130 is an absorbent terrycloth intermediate layer 140 having an extent corresponding to the crotch portion 124. The absorbent terrycloth intermediate layer 140 is sewn to the bodyside inner layer 130 along two stitching lines 142 and 144 immediately adjacent lateral edges 146 and 148 of the intermediate layer 140. The absorbent terrycloth intermediate layer 140 takes the particular form of two sublayers 150 and 152, and stitches 154 and 156 extend through both sublayers 150 and 152, as well as through the bodyside inner layer 130. The main torso part 112 additionally has a waterproof outer layer 160, which also has an extent corresponding to the extent of the main torso part 112. The waterproof outer layer 160 is sewn at the edges of the torso-receiving aperture 14 and the leg-receiving apertures 18 and 20. A suitable material for the waterproof outer layer 160 is a coated woven nylon fabric.

The swim diaper 110 of FIGS. 3 and 4 differs from the swim diaper 10 of FIGS. 1 and 2 in that a decorative fabric visible layer 170 has an extent greater than the extent of the main torso part 112, so as to extend partly down the legs of a wearer, in a boxer short configuration. Decorative designs 172 are printed on the decorative fabric visible layer 170. The decorative fabric visible layer 170 is sewn to the main torso part 112 only around the torso-receiving aperture 140, and hangs loosely. Accordingly, the swim diaper 110 of FIGS. 3 and 4 has the appearance of boxer-type swim trunks, but nevertheless serves the function of a swim diaper, in view of the main torso part 112 which includes the bodyside inner layer 130, the absorbent terrycloth intermediate layer 140, and the waterproof outer layer 160. The waterproof outer layer 160, in combination with the elastic-banded apertures 114, 118 and 120, serves to minimize the flow of liquids, such as urine and swimming pool water, between the inside and the outside of the swim diaper 110, particularly between absorbent terrycloth intermediate layer 140 and the outside environment.

A reusable swim diaper 10 of brief configuration (FIGS. 1 and 2) and a reusable swim diaper 110 of boxer short configuration (FIGS. 3 and 4) are specifically disclosed herein. Those are examples only, as the invention may be embodied in a variety of swim garment styles.

While particular embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A reusable swim diaper, comprising:
    a main torso part having an extent defined by an elastic-banded torso-receiving aperture at its upper end, a pair of elastic-banded leg-receiving apertures at its lower end, and a crotch portion generally between said leg-receiving apertures, said main torso part including
        a bodyside inner layer of breathable wick-away fabric, said bodyside inner layer having an extent corresponding to the extent of said main torso part,
        an absorbent terry cloth intermediate layer, and
        a waterproof outer layer, said waterproof outer layer having an extent corresponding to the extent of said main torso part;
    said layers being made of materials which are capable of withstanding laundering and are restored to substantially their original conditions by laundering.

2. The reusable swim diaper of claim 1, wherein said absorbent terry cloth intermediate layer has an extent corresponding to said crotch portion.

3. The reusable swim diaper of claim 1, which further comprises a decorative fabric visible layer over said main torso part, said decorative fabric layer also made of a material which is capable of withstanding laundering and is restored to substantially its original condition by laundering.

4. The reusable swim diaper of claim 3, wherein said decorative fabric visible layer has an extent corresponding to the extent of said main torso part.

5. The reusable swim diaper of claim 3, wherein said decorative fabric visible layer has an extent greater than the extent of said main torso part so as to extend part way down the legs of a wearer.

6. The reusable swim diaper of claim 1, wherein said absorbent terry cloth intermediate layer has a fabric weight of approximately 640 g/m$^2$.

7. The reusable swim diaper of claim 6, wherein said absorbent terry cloth intermediate layer has an extent corresponding to said crotch portion, and an area of approximately 200 cm$^2$.

8. The reusable swim diaper of claim 6, wherein said absorbent terry cloth intermediate layer comprises two sublayers each having a fabric weight of approximately 320 g/m$^2$.

9. The reusable swim diaper of claim 1, wherein said absorbent terry cloth intermediate layer comprises a polyester/polyamide fiber blend.

10. The reusable swim diaper of claim 6, wherein said absorbent terry cloth intermediate layer comprises a polyester/polyamide fiber blend.

11. The reusable swim diaper of claim 8, wherein said absorbent terry cloth intermediate layer comprises a polyester/polyamide fiber blend.

12. The reusable swim diaper of claim 1, wherein said bodyside inner layer comprises a knitted polyester fabric.

13. The reusable swim diaper of claim 1, wherein said waterproof outer layer comprises a coated woven nylon fabric.

14. The reusable swim diaper of claim 9, wherein said bodyside inner layer comprises a knitted polyester fabric.

15. The reusable swim diaper of claim 9, wherein said waterproof outer layer comprises a coated woven nylon fabric.

16. The reusable swim diaper of claim 14, wherein said waterproof outer layer comprises a coated woven nylon fabric.

17. A reusable swim diaper, comprising:
    a main torso part having an extent defined by an elastic-banded torso-receiving aperture at its upper end, a pair of elastic-banded leg-receiving apertures at its lower end, and a crotch portion generally between said leg-receiving apertures, said main torso part including
        a bodyside inner layer of breathable wick-away fabric, said bodyside inner layer having an extent corresponding to the extent of said main torso part, an absorbent terry cloth intermediate layer comprising a polyester/polyamide fiber blend and having a fabric weight of approximately 640 g/m$^2$, and a waterproof outer layer, said waterproof outer layer having an extent corresponding to the extent of said main torso part;

said layers being made of materials which are capable of withstanding laundering and are restored to substantially their original conditions by laundering.

18. The reusable swim diaper of claim 17, wherein said absorbent terry cloth intermediate layer has an extent corresponding to said crotch portion, and an area of approximately 200 cm$^2$.

19. The reusable swim diaper of claim 17, wherein said absorbent terry cloth intermediate layer comprises two sublayers each having a fabric weight of approximately 320 g/m$^2$.

* * * * *

UNITED STATES PATENT AND TRADEMARK OFFICE
CERTIFICATE OF CORRECTION

| | | |
|---|---|---|
| PATENT NO. | : 7,678,094 B1 | Page 1 of 1 |
| APPLICATION NO. | : 11/583367 | |
| DATED | : March 16, 2010 | |
| INVENTOR(S) | : Cannon et al. | |

It is certified that error appears in the above-identified patent and that said Letters Patent is hereby corrected as shown below:

Column 2, line 22, the words "order of" are deleted.

Column 2, lines 25-31, the entire paragraph is deleted.

Signed and Sealed this

Eighth Day of June, 2010

David J. Kappos
*Director of the United States Patent and Trademark Office*